US012748225B2

(12) United States Patent
Rahimi et al.

(10) Patent No.: US 12,748,225 B2
(45) Date of Patent: Sep. 29, 2026

(54) WIRELESS CHIPLESS PRINTED SENSOR TAG FOR REAL-TIME RADIATION STERILIZATION MONITORING

(71) Applicant: Purdue Research Foundation, West Lafayette, IN (US)

(72) Inventors: Rahim Rahimi, West Lafayette, IN (US); Ulisses Heredia Rivera, Hillsboro, OR (US); Sarath Gopalakrishnan, Santa Rosa, CA (US)

(73) Assignee: Purdue Research Foundation, West Lafayette, IN (US)

( * ) Notice: Subject to any disclaimer, the term of this patent is extended or adjusted under 35 U.S.C. 154(b) by 167 days.

(21) Appl. No.: 18/224,913

(22) Filed: Jul. 21, 2023

(65) Prior Publication Data

US 2024/0168184 A1 May 23, 2024

Related U.S. Application Data

(60) Provisional application No. 63/391,149, filed on Jul. 21, 2022.

(51) Int. Cl.
*G01T 1/02* (2006.01)
*A61L 2/081* (2026.01)
(Continued)

(52) U.S. Cl.
CPC ................ *G01T 1/24* (2013.01); *A61L 2/081* (2013.01); *A61L 2/28* (2013.01); *G01T 1/026* (2013.01);
(Continued)

(58) Field of Classification Search
CPC ...................................................... G01T 1/026
See application file for complete search history.

(56) References Cited

U.S. PATENT DOCUMENTS 6,398,710 B1 * 6/2002 Ishikawa ................ G01T 1/026 250/484.5
2002/0040968 A1 * 4/2002 Black ........................ A23L 5/30 250/370.07

(Continued)

OTHER PUBLICATIONS

Armenante, P. M. et al., Sterilization Processes in the Pharmaceutical Industry, Chapter 14 In Chemical Engineering in the Pharmaceutical Industry, Drug Product Design, Development and Modeling, Second Edition, 2019, John Wiley & Sons, Inc, Hoboken, NJ, USA, pp. 311-379; Published 2019 by John Wiley & Sons, Inc.

(Continued)

*Primary Examiner* — Uzma Alam
*Assistant Examiner* — Shun Lee
(74) *Attorney, Agent, or Firm* — Purdue Research Foundation

(57) ABSTRACT

A system may receive a package previously irradiated for sterilization. The package may have a sensor comprising a reference tag and sensing tag at least partially coated with a material comprising poly(3,4-ethylenedioxythiophene) polystyrene sulfonate (PEDOT:PSS) and Polyurethan (PU). The system may scan the sensing tag and the reference tag. The system may determine, based on radio frequency (RF) signals reflected from the sensing tag and reference tag, the sensor is exposed to radiation. The system may output a quality measure indicative of the sensor being exposed to radiation.

15 Claims, 9 Drawing Sheets

(51) Int. Cl.
*A61L 2/28* (2006.01)
*G01T 1/24* (2006.01)

(52) U.S. Cl.
CPC ....... *A61L 2202/14* (2013.01); *A61L 2202/18* (2013.01)

(56) References Cited

U.S. PATENT DOCUMENTS

| | | | | |
|---|---|---|---|---|
| 2005/0007239 | A1* | 1/2005 | Woodard | G01D 21/00<br>340/10.2 |
| 2005/0093701 | A1* | 5/2005 | Hollon | G06K 19/07784<br>235/491 |
| 2009/0108993 | A1* | 4/2009 | Forster | G06K 19/0724<br>340/10.1 |
| 2014/0360269 | A1* | 12/2014 | Burghardt | G01P 15/02<br>73/535 |
| 2016/0155041 | A1* | 6/2016 | Ozaki | H01Q 1/2208<br>235/488 |
| 2017/0342213 | A1* | 11/2017 | Green | C08L 83/04 |

OTHER PUBLICATIONS

IAEA (International Atomic Energy Agency) Annual Report 2008, Oct. 2008 for the period Jan. 1 to Dec. 31, 2008; GC(53)/7; 129 pgs.

Clough, R. L., High-energy radiation and polymers: A review of commercial processes and emerging applications. Nuclear Instruments Methods in Physics Research B, NIMB Beam Interations with Materials & Atoms, 2001, vol. 185, 2001, pp. 8-33.

Ilčin, M. et al., FT-IR study of gamma-radiation induced degradation of polyvinyl alcohol (PVA) and PVA/humic acids blends. J. Radioanal. Nucl. Chem., 2010, vol. 283, pp. 9-13; published online Aug. 28, 2009.

Sousa, A. R. et al., The stress cracking behavior of poly(methyl methacrylate) after exposure to gamma radiation. Polymer Degradation and Stability, vol. 92, 2007, pp. 1465-1475; available online May 21, 2007.

Gorna, K. et al., The effect of gamma radiation on molecular stability and mechanical properties of biodegradable polyurethanes for medical applications. Polymer Degradation and Stability, vol. 79, 2003, pp. 465-474.

Devic, S., Radiochromic film dosimetry: Past, present, and future. Physica Medica, vol. 27, 2011, pp. 122-134; available online Nov. 2, 2010.

Alyahyawi, A. et al. Off-the-shelf thermoluminescent silica glass media for use in medical diagnostic dosimetry applications. Applied Radiation and Isotopes, vol. 178, 2021, 109953, pp. 1-6; available online Sep. 16, 2021.

Rosenfeld, A. B. et al., Semiconductor dosimetry in modern external-beam radiation therapy. Physics in Medicine & Biology, vol. 65, 2020, 65, 16TR01, pp. 1-38; published Aug. 14, 2020.

Collura, G. et al., Analysis of the response of PVA-GTA Fricke-gel dosimeters with clinical magnetic resonance imaging. Nuclear Instruments and Methods in Physics Research B, vol. 414, 2018, pp. 146-153; available online Jun. 22, 2017.

Shamim, A. et al., Wireless Dosimeter: System-on-Chip Versus System-in-Package for Biomedical and Space Applications. IEEE Transactions on Circuits and Systems—II: Express Briefs, vol. 55, No. 7, Jul. 2008, pp. 643-647; first published Apr. 16, 2008.

Francik, A., The Microwave Autodyne Gunn Oscillator as a Simple Detector of EPR Signal for Food-Irradiation Dozymeter. In 14th International Conference on Microwaves, Radar and Wireless Communications, Mikon—2002, Conference Proceedings (IEEE Cat. No. 02EX562), 2002, vol. 1, pp. 103-106.

Li, Y. et al., Demonstration of a Passive Wireless Radiation Detector Using Fully-Depleted Silicon-on-Insulator Variable Capacitors. IEEE Transactions on Nuclear Science, vol. 64, No. 1, Jan. 2017, pp. 544-549; date of publication Nov. 1, 2016.

Heo, S. Y. et al., Wireless, battery-free, flexible, miniaturized dosimeters monitor exposure to solar radiation and to light for phototherapy. Science Translational Medicine, 2018, 10, eaau1643, Dec. 5, 2018; pp. 1-12.

Kwon, K. et al., Miniaturized, light-adaptive, wireless dosimeters autonomously monitor exposure to electromagnetic radiation. Science Advances, 2019, 5:eaay2462, Dec. 13, 2019; pp. 1-9.

Brinker, K. et al., Bistatic Microwave Sensor for In-Situ Composite Inspection and Structural Health Monitoring. 2021 IEEE Instrumentation and Measurement Technology Conference (I2MTC), 978-1-7281-9539-1/21, 2021.

Zareei, A. et al., Highly Conductive Copper-Silver Bimodal Paste for Low-Cost Printed Electronics. ACS Applied Electronic Materials, 2021, vol. 3, pp. 3352-3364; published Aug. 13, 2021.

Gopalakrishnan, S. et al., Battery-Less Wireless Chipless Sensor Tag for Subsoil Moisture Monitoring. IEEE Sensors Journal, vol. 21, No. 5, Mar. 1, 2021, pp. 6071-6082; date of publication Nov. 19, 2020.

* cited by examiner

WIRELESS CHIPLESS PRINTED SENSOR TAG FOR REAL-TIME RADIATION STERILIZATION MONITORING

CROSS REFERENCE TO RELATED APPLICATIONS

This application claims the benefit of U.S. Provisional Application No. 63/391,149 filed Jul. 21, 2022, the entirety of which is herein incorporated by reference in its entirety.

TECHNICAL FIELD

This disclosure relates to radiation sensors and, in particular, to printable radiation sensors.

BACKGROUND

To ensure that the health equipment does not spread any infectious disease, virus, or pathogens to patients, proper sterilization and disinfection of all pharmaceutical devices (e.g., reusable, and single-use bioreactors). Modern disinfection approaches include filtration, chemical, thermal, and radiation sterilization. However, due to the temperature and chemical sensitive nature of various single-use health instruments such as masks, surgical gloves, and syringes, radiation sterilization technique is preferred over thermal and chemical sterilization methods. In pandemic conditions, when the whole world requires appropriate disinfection of all single-use items at a rapid and large scale, fast radiation sterilization technique is chosen over the slow disinfection approaches. Additionally, the gamma radiation sterilization can easily eliminate microorganisms from packaged medical devices by the exposure of high-energy ionizing radiations.

BRIEF DESCRIPTION OF THE DRAWINGS

The embodiments may be better understood with reference to the following drawings and description. The components in the figures are not necessarily to scale. Moreover, in the figures, like-referenced numerals designate corresponding parts throughout the different views.

DETAILED DESCRIPTION

Figure 1:
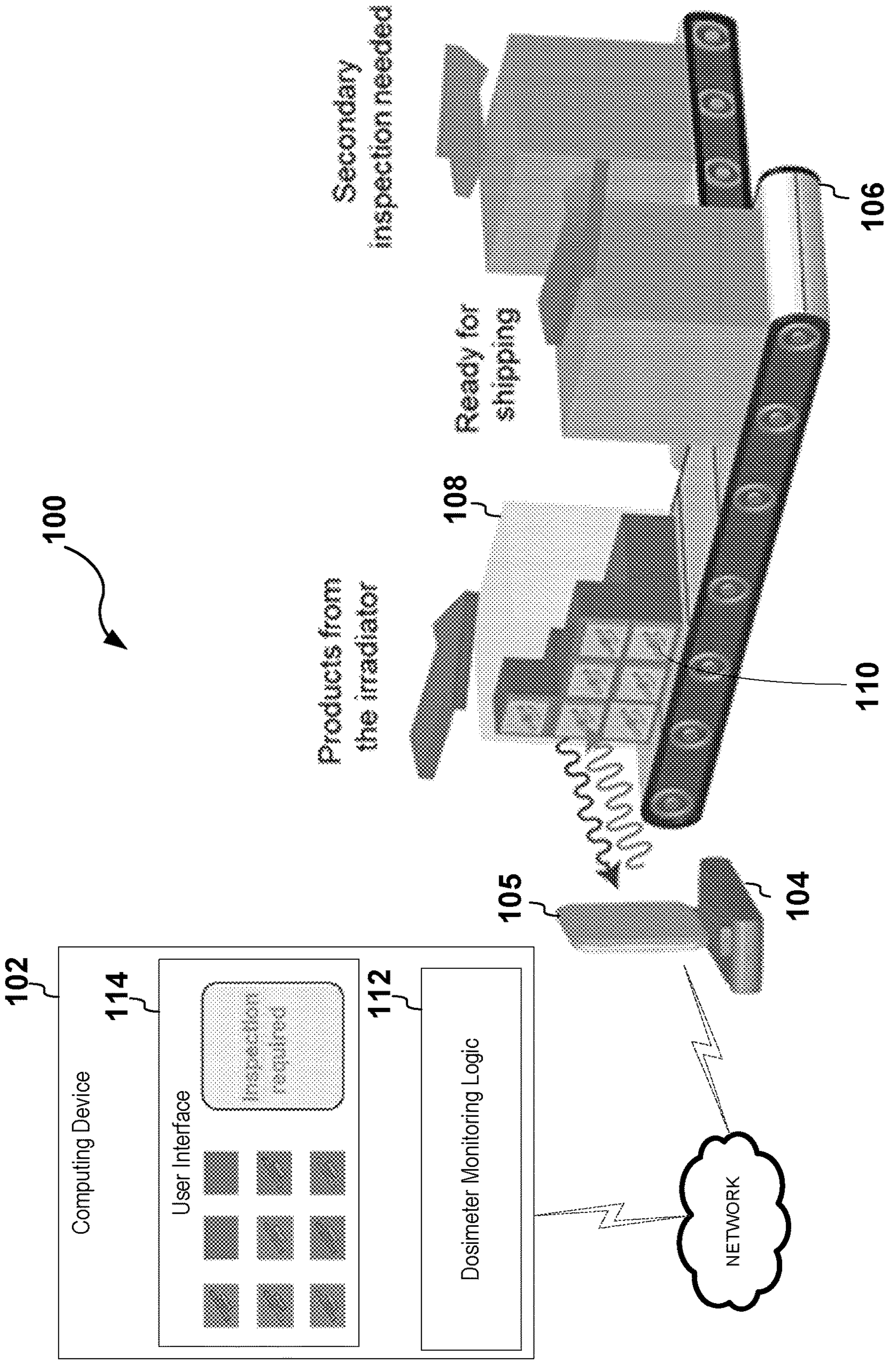
FIG. 1 illustrates a first example of sterilization monitoring system.

Although the gamma radiation sterilization approach has been widely employed in over 200 countries for pharmaceutical packaging, there is an increasing demand for estimating the dosage of gamma rays during sterilization for several reasons. Overexposure to gamma-ray radiation can lead to deleterious effects on the mechanical and chemical properties of the materials used in the health devices thereby affecting the quality of the products. On the other hand, underexposure can lead to incomplete elimination of microorganisms and viruses from the health equipment. Therefore, to prevent the under- and over-exposure of medical instruments, accurate detection of gamma radiation is extremely important in pharmaceutical packaging. Currently, various techniques including radiochromic films (RCFs), thermoluminescent, chemical, and semiconductor dosimeters have been used in pharmaceutical packaging for monitoring the sterilization process. Although RCFs are east to use films that change the color of the emulsion layer upon absorption of gamma rays, they are moisture sensitive and time taking processes. Thermoluminescent dosimeters are small and convenient, but they need careful conditioning, individual calibration, and a long read-out time after irradiation. Similarly, semiconductors dosimeters can read out immediately; however, they are costly and dependent on energy as well as dose rate and temperature during sterilization. Likewise, colorimetric dosimeters are inexpensive and easy to manufacture; however, in situ examination of the radiation dosage of a product inside a package is unrealistic with colorimetric techniques as they require visual inspection of the films. For instance, Fricke dosimeters can only be used for 50 to 200 Gy range and thus, are not suitable for sterilization environments. In addition to wireless dosimeters, a few wired dosimeters have also been used for gamma-ray detection, but they are expensive and not suitable for sterilization applications.

Accordingly, there exists a need to attach a wireless sensor to an individual package stacked inside the large container that can monitor the gamma radiation dosage received by a particular package during the sterilization process. Moving toward automation which involves packages being carried through conveyor belts and disinfected in real-time without accessing the sensor embedded in the package, additional technical challenges become prevalent. Because of the high variability in the material used for the fabrication of packed health instruments, there could be a large variability between levels of exposure that each device will receive during the sterilization.

Existing wireless dosimeters involve transducers or sensors that require active batteries or chips inside them which increases the manufacturing cost. Recently, batteryless wireless dosimeters have been introduced to meet the demand for low-cost, real-time, remote detection of high dosage gamma radiation to facilitate automated processing and warehousing of medical devices. However, the reported sensors are not electronics-free and the ionizing radiations can damage the electronic components of the device. Therefore, the development of an economic, real-time chipless wireless dosimeter that can overcome the aforementioned limitations is highly desired. Passive chipless wireless sensors have been widely used for structural health monitoring, humidity sensing, and agricultural applications. However, their potential use in radiation sensing has not been explored in previous studies.

The system and methods described here provide a low-cost, chipless, and wireless radiation sensor (which s interchangeably referred to as a dosimeter herein) that can be manufactured by using scalable printing technologies. A radiation sensitive composite material made of poly(3,4-ethylenedioxythiophene) polystyrene sulfonate (PEDOT: PSS) and Polyurethan (PU) polymers following the percolation theory coupled with a far-field passive chipless platform was developed in order to detect gamma radiation exposure up to 40 kGy or more. The reported sensor can be potentially used to perform real-time measurements of hermetically sealed medical products with a non-invasive reader. Moreover, encoded chipless sensors can provides us traceability and trackability which enhance the quality control of the medical devices.

FIG. 1 illustrates a first example of a sterilization monitoring system 100. The system may include a computing device 102 and a network analyzer 104, such as a vector network analyzer (VNA) in communication with an antenna 105. A conveyer belt 106 or some other conveyance machine may move monitored package(s) 108 proximate to the network analyzer. The monitored package(s) may include one or more package that includes a wireless radiation sensor 110. In some examples, monitored packages affixed with radiation sensors may be grouped together and placed inside a larger package.

The wireless radiation sensor 110 may provide chipless and wireless sensing by combining the principles of electrical percolation theory and far-field backscattering technique. The wireless radiation sensor 100 operating in a differential configuration may include a radiation sensitive coating on the sensing tag and a radiation insensitive silver-based reference tag manufactured using scalable printing technologies.

A radiation sensitive functional material based on PEDOT: PSS/PU composites with electrical properties in the transition percolation area may provide an impedance change (i.e. 375%) after of radiation exposure (i.e. 40 kGy). Upon gamma radiation exposure, the chemical structure of PEDOT chains exhibit alterations including amorphism and chain scission which leads to a decrease in its electrical conductivity. In various experimentation, it was found that the radiation sensor may be wirelessly read from a distance of 10 cm and with an amplitude shift of 3.2 dB after 40 kGy radiation exposure with a linear radiation sensitivity of 0.1 dB/kGy. These findings demonstrate the feasibility of the radiation sensor in real-time radiation sterilization monitoring of medical devices and other potential applications in the agriculture and food industry. In practice, the radiation sensor may be tuned for the particular application The computing device 102 may include a dosimeter monitoring logic 112 which may communicate with the network analyzer 104 to perform analysis and monitoring of the radiation sensors. Alternatively or in addition, the dosimeter monitoring logic may itself include network analysis capabilities and communicate directly with an antenna. Based on an analysis of the signals received from the radiation sensor, packages may be assigned a quality measure, or even a simple binary value which indicates a pass or fail qualification. Alternatively or in addition, the quality measure may include a radiation measurement or some other measurement indicative of radiation exposure further described herein. The dosimeter monitoring logic 112 may cause the quality measurement to be output. This may involve displaying the measurement on a graphical user interface, communicating the measurement over a network, or storing the measurement in memory, Alternatively or in addition, the dosimeter monitoring logic 112 may cause a monitored package, or bundled group of monitored packages, to be re-routed for further inspection if one or more radiation sensors indicate the packed is compromised.

The computing device 102 may include a workstation, mobile device, or even cloud-based system. In some examples the computing device 102 may include a graphical user interface, which may display information corresponding to the radiation sensors and packages, including package identifiers and other information that identifies the package, quality measurements derived form measurements obtained from the radiation sensors.

Figure 2:
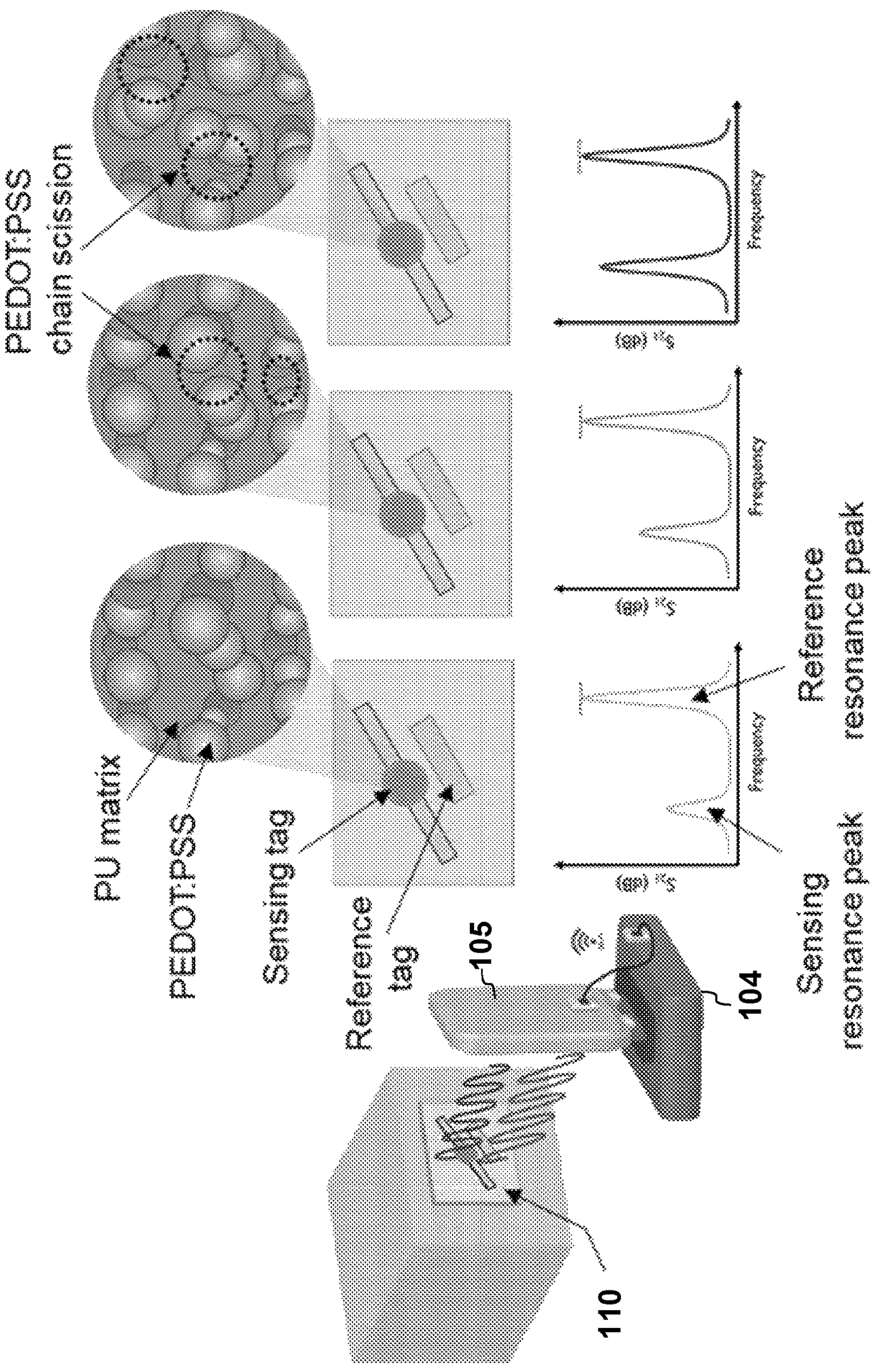
FIG. 2 illustrates the operational principle of a radiation sensor radiation sensor.

FIG. 2 illustrates the operational principle of the wireless radiation sensor 110. The wireless radiation sensor involves two different technologies to achieve wireless radiation detection, a radiation-sensitive PEDOT: PSS/PU composite material and far-field printed tags. The radiation sensor comprises a sensing tag having a silver printed interdigitated electrode (IDE) coupled with a highly radiation sensitive PEDOT: PSS/PU composite film and a printed silver reference tag.

An antenna may send an interrogation signal which is backscattered by the radiation sensor surface. The backscattered signal collected by the antenna provides information about changes in the amplitude of resonance peaks corresponding to the sensing and reference tag which are used for tracking the radiation exposure. Upon radiation exposure, the electrical properties of the sensing tag may change due to chain scission in the composite material whereas the electrical properties of the reference tag remain the same.

Consequently, the backscattered signal read by the antenna is sent to a vector network analyzer (VNA) for wireless measurement, which shows a significant change in the amplitude of the resonance peak that corresponds to the sensing tag and no change for the peak that corresponds to the reference tag. Since environmental variables such as moisture, temperature, and background noise can affect the amplitude of both the sensing and the reference tag resonance peaks, the difference between these two peaks is used to measure the amount of radiation exposure.

Figure 3A:
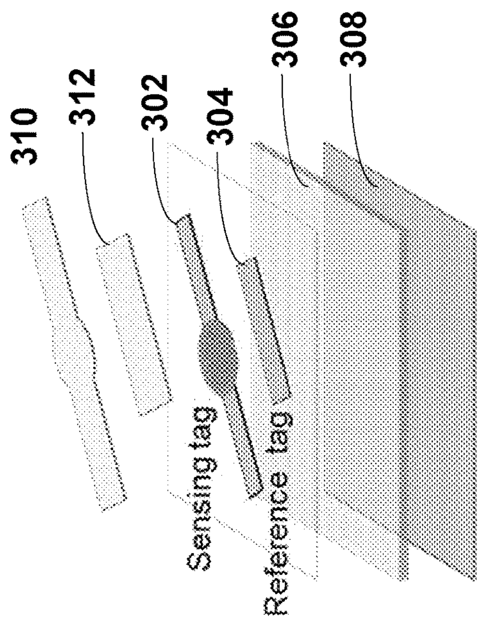
FIG. 3A-B illustrates an example of an exploded view of a printed radiation sensor and a fabrication process.
Figure 3B:
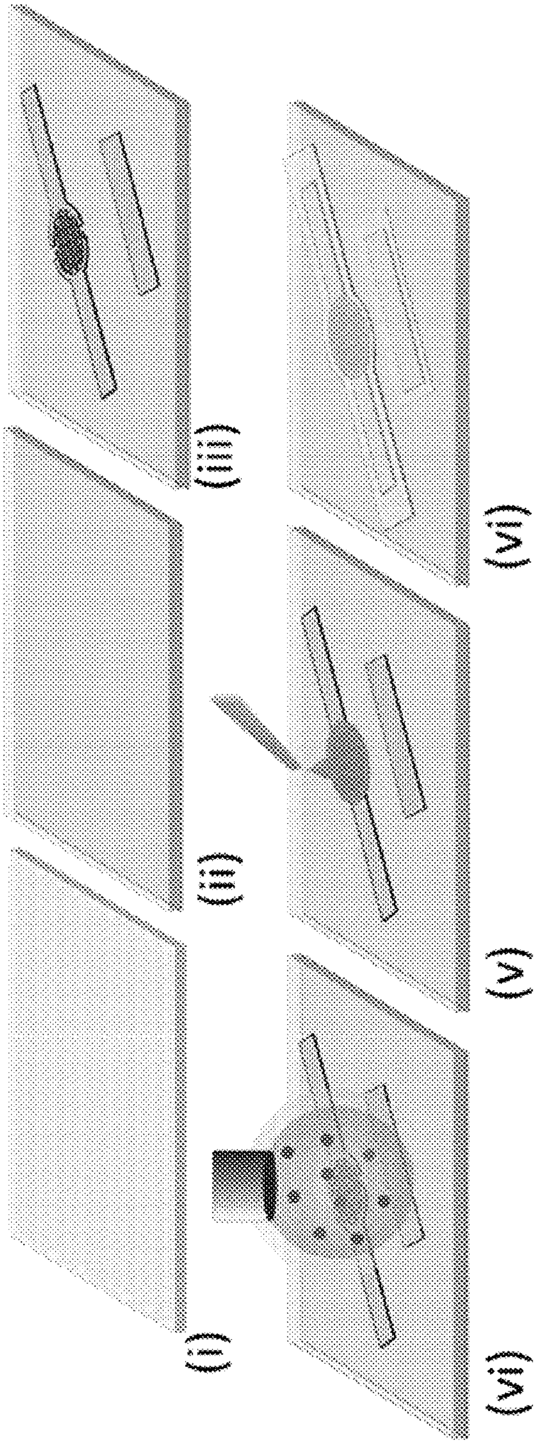

FIG. 3A-B illustrates an exploded view of a printed radiation sensor and an example of a fabrication process. FIG. 3A illustrates a schematic design of an exploded view of the radiation sensor. The radiation sensor may include a tag layer having a sensing tag 302 and a reference tag 304. The sensing tag may include comprise a silver printed interdigitated electrode (IDE) The tag layer and/or the sensing tag and reference tag may be received by a substrate layer 306. The substrate layer 306 may include an acrylic. The substrate layer 306 may be positioned on a metallic layer 308. The metallic layer 308 may include, for example, copper. In some examples, the metallic layer 308 may include a metallic tape which has adhesive on one or both sides. This, the metallic layer 308 may adhere to both the acrylic substrate and the package surface onto which the radiation sensor is placed. A passivation layer 310, 312 may be placed over the reference tag and/or sensing tag. In some examples, the passivation layer may separately or together cover the sensing tag and reference tag. Ideally, the sensing tag and reference tag are insulated from each other by the passivation layer(s).

FIG. 3B illustrates the radiation sensor at various stages of fabrication. The fabrication process may include (i) laser cutting an acrylic substrate; (ii) attaching copper tape to the acrylic substrate; (iii) Screen printing a reference tag and interdigitated electrode (IDE) structure of the sensing tag. (iv) Plasma treating of printed tags. (v) Casting a PEDOT: PSS/PU composite onto the IDE area of the sensing tag; and (vi) Passivating of printed tags with silicone.

To produce low-cost radiation sensors that can be placed inside the individually packaged products, the wireless radiation sensor may be manufactured by employing scalable techniques for printed electronics, such as those shown in FIG. 3B. A substrate, such as an acrylic substrate, may be laser cut. Then, the radiation sensor substrate may be prepared by attaching copper tape to the backside of the acrylic sheet (step i and ii). Next, the silver reference tag and interdigitated structure of the sensor tag may be printed onto a polyethylene terephthalate (PET) sheet by screen printing and dried. In various experimentation, the drying was performed with a conventional oven at 120° C. for 5 min, though other temperatures and lengths may also be suitable. (step iii). Once dried, the tags were added to the substrate and subjected to plasma treatment for 45 s to improve its wettability and the adhesion to the PEDOT: PSS/PU composite (step iv). Finally, an optimized amount of PEDOT: PSS/PU solution (50 μL) was cast onto the interdigitated area of the sensor tag and dried at 50° C. in a hot plate for 50 s (step v). Further, the sensor and reference tag were passivated with silicone to protect against silver oxidation, environmental moisture, and surface scratches (step vi). A detailed fabrication process is further described in the experimental section.

Figure 4A:
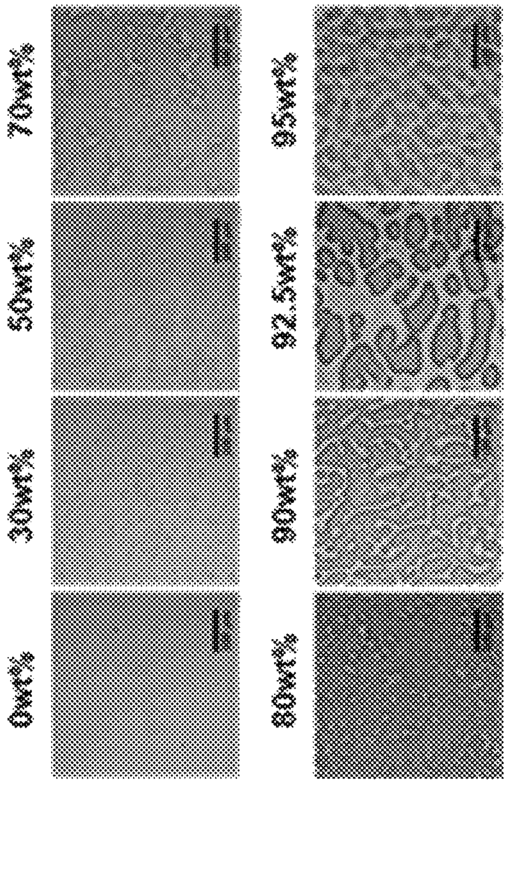
FIG. 4A-B illustrates microscopic morphology and electrical properties of printed radiation sensors.
Figure 4B:
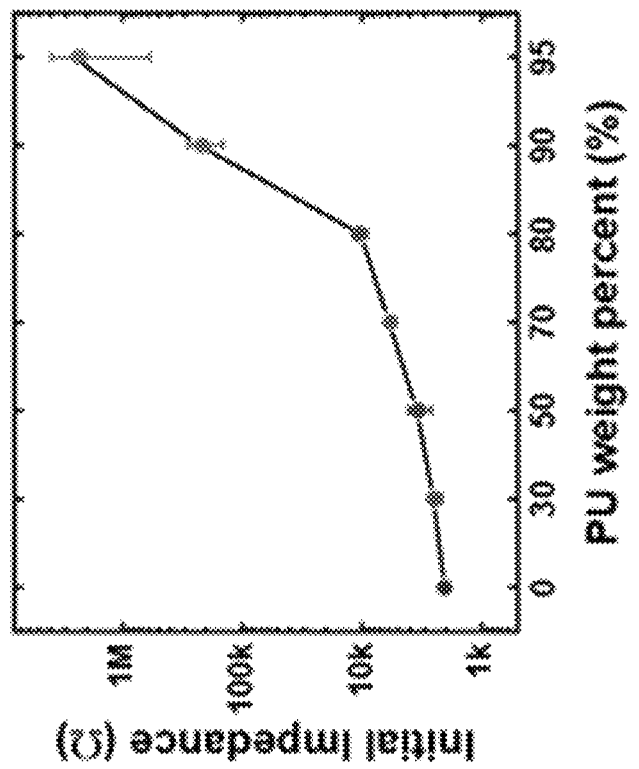

FIG. 4A-B illustrates microscopic morphology and electrical properties of printed radiation sensors. FIG. 4A illustrates optical micrographs of PEDOT: PSS/PU composites with different PU content. PEDOT: PSS-rich regions are shown in dark blue while the PU-rich regions are shown in light gray. FIG. 4B illustrates the impedance of radiation sensors prepared using different PU weight percentages.

It has been reported that the electrical conductivity of conductive polymer composites such as PEDOT: PSS/PU depends upon several factors including the shape, size, concentration of conductive fillers (PEDOT: PSS polymer chains), and the microstructure formed with the polymer matrix (PU). Therefore, to study the relationship between morphology and conductivity of PEDOT: PSS/PU composites, a series of optical micrographs were taken at different PEDOT: PSS/PU ratios. It can be observed from FIG. 4A that the PU-rich regions (light gray area) in the PEDOT: PSS matrix (dark blue area) gradually increased as the PU content was increased from 0 wt % to 95 wt %. Since waterborne PU dispersion self-assembles, the initially small and dispersed PU particles start recombining to form a well-connected PU network that simultaneously hindered the connectivity among conductive PEDOT: PSS-rich regions. Thus, these changes in the polymer composite morphology might show a significant effect on the electrical behavior of the printed radiation sensors. For the proof-of-concept, the impedance of radiation sensors prepared using different PU weight percentages was recorded (FIG. 4B) and observed that the increasing PU content led to decreasing conductivity of PEDOT: PSS/PU composites. However, this increment in electrical impedance did not follow a linear behavior. It was noticed that the PU content below 80 wt % gradually increased the impedance with the addition of PU into the PEDOT: PSS matrix whereas from 80 wt % to 90 wt %, the electrical impedance rapidly increased due to a significant disruption in the conductive network formed by PEDOT: PSS-rich regions. The further addition of PU content (95 wt %) severely increased the polymer composite impedance to the order of 106 Ohms revealing that the conductive network reached the percolation threshold. Since the impedance value of PEDOT: PSS/PU composite with 90 wt % PU content falls in the percolation transition area, small changes in the connectivity of conductive paths would lead to a high change in the conductivity values required to develop a highly sensitive radiation sensor. Therefore, the PEDOT: PSS/PU composite with 90 wt % PU content was chosen for further sensing experiments. Also, the effect of silicone passivation on the impedance values of the radiation sensor prepared using final composite was investigated and found negligible.

Figure 5A:
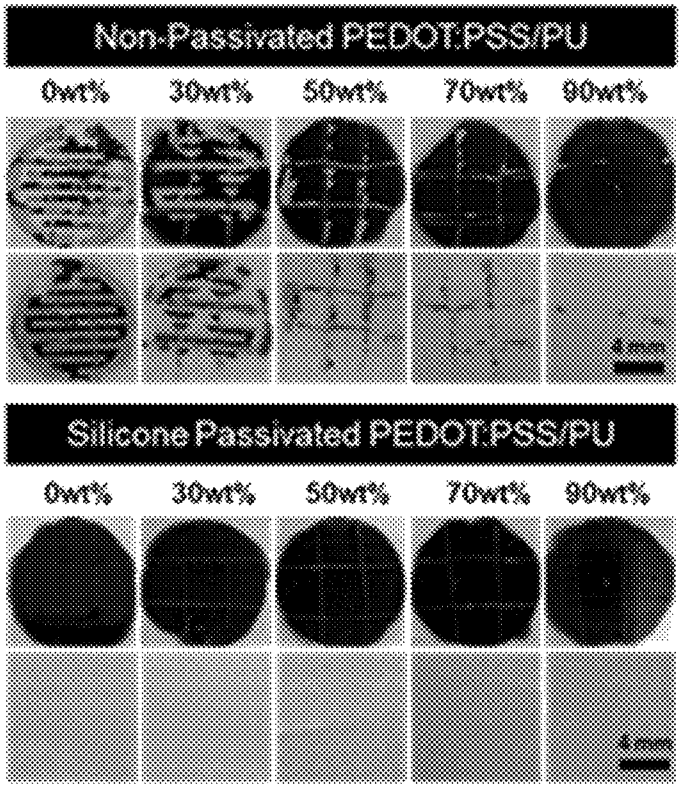
FIG. 5A-B illustrate a radiation sensor under a peeling test and a chart showing related results.
Figure 5B:
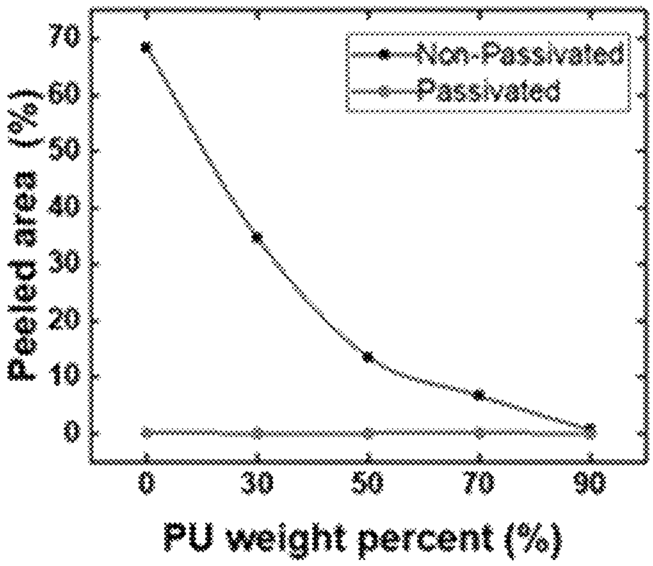

FIG. 5A illustrates the radiation sensor under a peeling test of PEDOT: PSS/PU composites. The macroscopic images of leftover (of the films) and peel out (on the tape) area of non-passivated radiation sensors (above) and silicone passivated radiation sensors (below). FIG. 5B illustrates a chart showing peeled area vs PU content of non-passivated and silicone passivated radiation sensors.

The adhesive strength of composite polymeric materials also plays an important role to examine their potential for sensing application, because a poor adhesion can induce delamination and premature failure of the radiation sensors. In this regard, a peeling test of composites having different PU wt % (ranging from 0 to 90%) was performed by making grids on the top of films and using pressure-sensitive tape. To make a qualitative analysis, the peeled area was examined using ImageJ software. The macroscopic images of the leftover (of the films) and peel-out (on the tape) area is shown in FIG. 5A. It can be visualized from FIG. 5*a* that the adhesive behavior of PEDOT: PSS/PU composites are highly dependent on the content of PU present in the composite. FIG. 5B shows the qualitative analysis of the peeling test, where it can be observed that 68.48% area was peeled off from the films made of neutralized PEDOT: PSS, and only 0.59% area was removed from the film having 90 wt % PU. This drastic increase in adhesive strength between the printed electrodes and PEDOT: PSS/PU films can be attributed to the higher number of polar groups found in waterborne polyurethane dispersions that led to higher polar force interactions with the plasma-treated PET substrate. Moreover, it can also be noticed that the incorporation of a silicone passivation layer not only prevented the oxidation of the silver electrodes but also avoids the delamination of PEDOT: PSS/PU films. Additionally, these results also support the selection of PEDOT: PSS/PU composite with 90 wt % PU content for further sensing experiments.

Figure 6B:
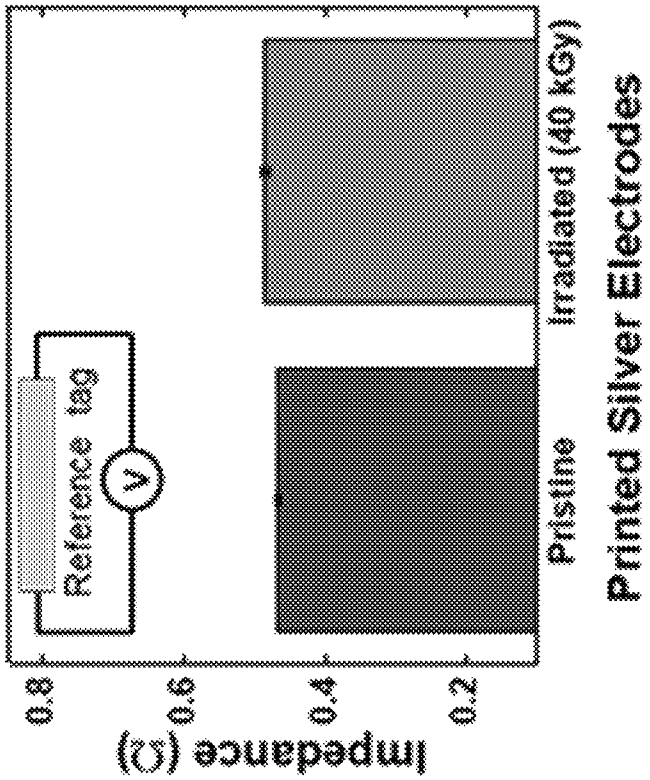
FIG. 6 A-B illustrate a chart showing impedance changes of sensing and reference tags of radiation sensors according to various embodiments.
Figure 6A:
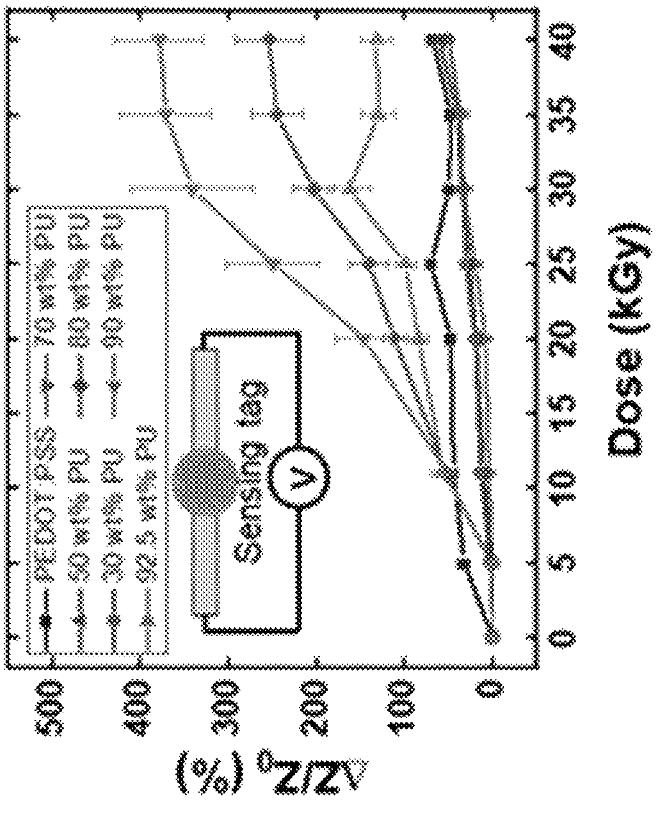

FIG. 6A illustrates a chart showing impedance changes of PEDOT: PSS/PU-based radiation sensors with different PU content. FIG. 6B illustrates a chart showing impedance of pristine and irradiated (40 kGy) silver printed reference tags.

To evaluate the radiation sensing performance of PEDOT: PSS/PU composites, all devices prepared using different PU content were exposed from 0 to 40 kGy. It can be observed from FIG. 6A that the composites around the percolation threshold exhibited high sensitivity in the studied dose range. Specifically, the PEDOT: PSS/PU composite with 90 wt % PU exhibited the highest sensitivity reaching about 375% in relative impedance change at 40 kGy. The further increase in PU content to 92.5 wt % significantly reduced the relative impedance change and thus results in the poor sensitivity of the device. In addition, the changes in the electrical properties of printed reference tags upon radiation exposure were also investigated and shown in FIG. 6B. It can be seen that no significant difference in the impedance of printed reference tags was found even after a gamma radiation exposure of 40 kGy. Therefore, these findings support the use of silver-printed tags as a reference for radiation sensing.

Figure 7B:
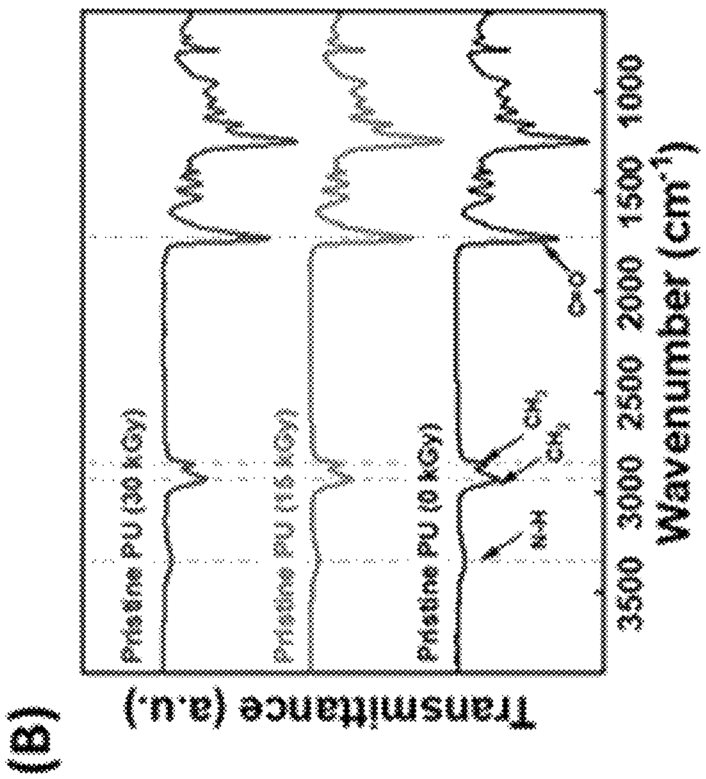
FIG. 7A-B illustrates charts showing the FTIR spectra of radiated and non-radiated PEDOT: PSS films and PU films.
Figure 7A:
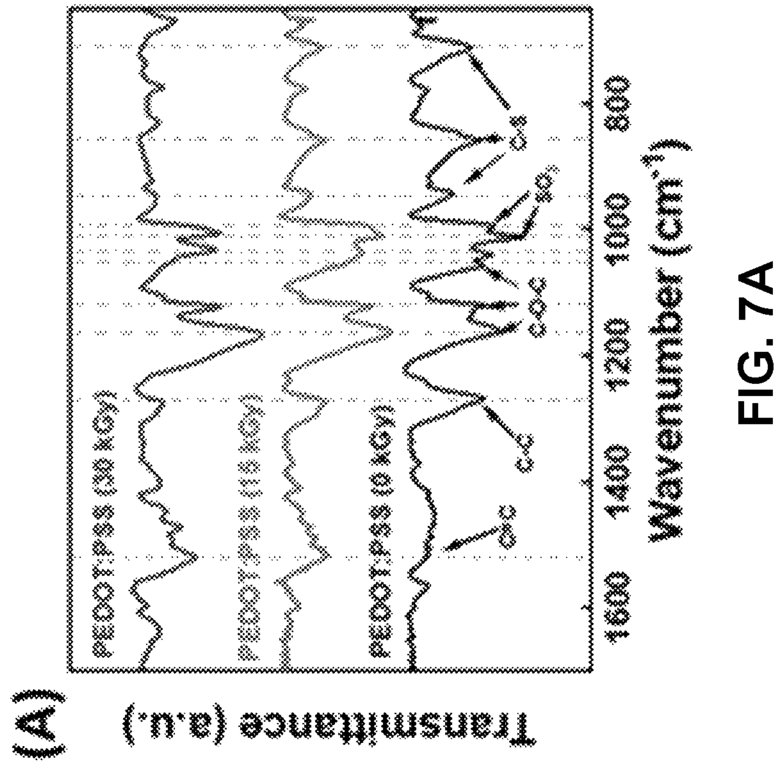

FIG. 7A illustrates charts showing the FTIR spectra of radiated and non-radiated PEDOT: PSS films. FIG. 7B illustrates charts showing the FTIR spectra of radiated and non-radiated PU films.

To confirm the sensing mechanism through PEDOT: PSS chain scission, the FTIR spectra of both PEDOT: PSS and PU films at different radiation doses (0 kGy, 15 kGy, and 30 kGy) was collected and shown in FIGS. 7A-B respectively. FIG. 7A shows the FTIR spectra for PEDOT: PSS samples in the range from 1900 to 650 $cm^{-1}$. The presence of conjugation structure plays an important role to define the conductive nature of conductive polymers. This conjugation structure of PEDOT was confirmed by the clear presence of the bands associated with C═C and C—C stretching vibrations of the thiophene ring at 1524 and 1271 $cm^{-1}$, respectively. Additional bands noticed at wavenumbers 946, 858, and 710 $cm^{-1}$ were ascribed to the stretching vibrational modes of the C—S bond that exist in the thiophene ring. Further, the C—O—C bond stretching caused by the ethylenedioxy group was assigned to the peaks located at wavenumbers 1161,1120 and 1057 $cm^{-1}$. The additional peaks at 1038 and 1010 $cm^{-1}$ were attributed to the stretching vibrational mode of sulfonic acid groups ($SO_3$) present in the chemical structure of PSS. It was observed that in contrast to non-radiated PEDOT (0 kGy), the bands associated with the C═C and C—C bonds broaden upon gamma radiation exposure, revealing chemical changes attributed to amorphism and chain scission of the conjugate structure of PEDOT chains, hence hindering its electrical conductivity. Moreover, the significant decrease in the intensity of the bands associated with the C—S and C—O—C bonds after radiation exposure can also be attributed to the chain scission which led to a significant decrease in conductivity.

FIG. 7B shows the FTIR spectra of PU films at different radiation doses. The characteristic broad N—H stretching band of PU was identified between 3200 to 3500 $cm^{-1}$. Similarly, the bands at wavenumbers 2935 and 2861 $cm^{-1}$, were associated with the symmetric and asymmetric stretching of $CH_2$ and $CH_3$, respectively. Another strong peak at wavenumber 1735 $cm^{-1}$ is assigned to the stretching of C═O bond present in the PU structure. In contrast to PEDOT: PSS, no significant change in the chemical structure of PU was noticed even up to 30 kGy radiation exposure. Therefore, these findings enable us to conclude that the change in conductivity is mostly happened due to the chain scission of PEDOT: PSS chains.

Furthermore, to investigate the variation in the amplitude of resonance with various values of conductivity of PEDOT: PSS and validate the experimental findings, simulations were performed using CST Microwave Studio. For the simulations, the radiation sensor implemented in CST Microwave studio consisted of an acrylic substrate of size 10 cm×10 cm×3 mm with a copper-based ground plane of size 10 cm×10 cm×0.1 mm. The sensing tag was implemented with an IDE structure in the middle and microstrip extensions of length 4 cm on either side. The PEDOT: PSS layer on the sensing tag was of radius 6 mm and was set to a dielectric constant of 2. Since the resonant frequency is a function of the length of the tag, the reference tag was set to a length of 3 cm in order to separate the resonant frequency of the sensing tag from the resonant frequency of the reference tag thereby avoiding an overlap between them. The sensing tag and the reference tag were separated by 1.5 cm to prevent mutual coupling while ensuring that their position within the beamwidth of the reader antenna to obtain maximum reflections. A plane wave approximation with radiation boundary conditions was used to configure the simulations. The conductivity of PEDOT: PSS was varied using the values observed in measurements in accordance with the changes in the radiation dosage.

Figure 8A:
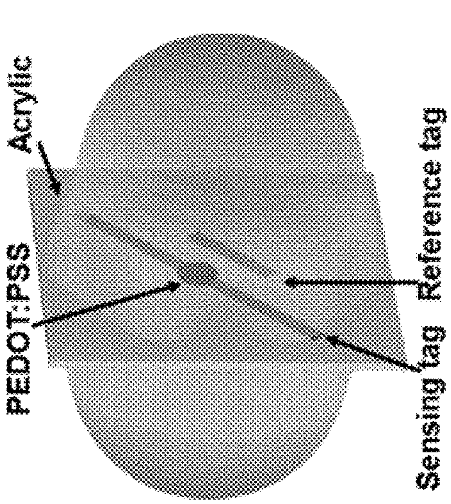
FIG. 8A-F illustrate simulation and experimental results from wireless measurements on a radiation sensor.
Figure 8B:
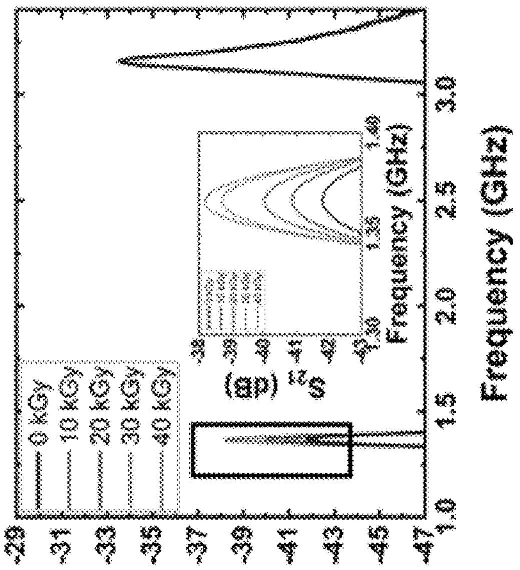
Figure 8C:
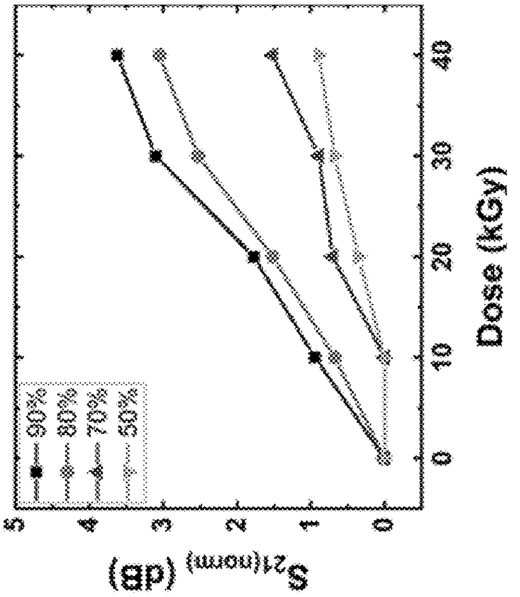
Figure 8D:
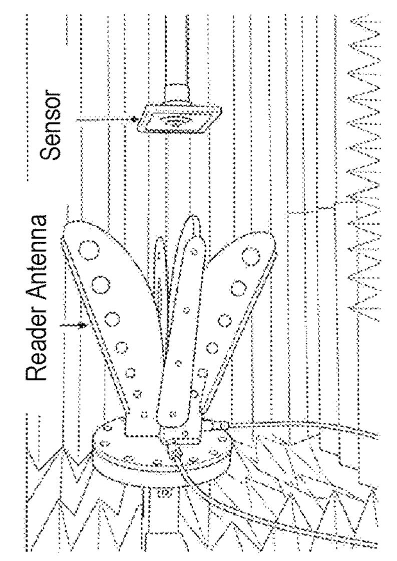
Figure 8E:
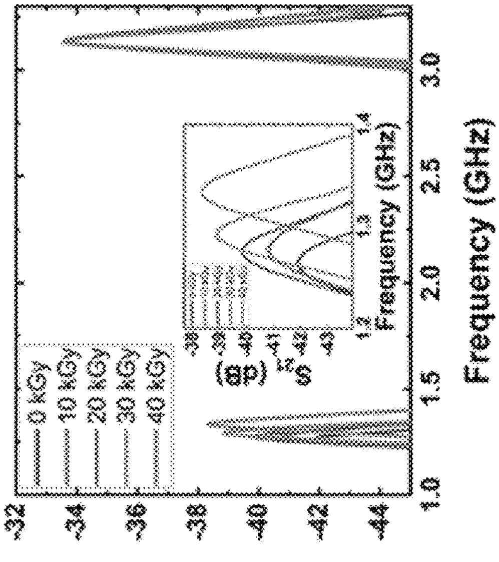
Figure 8F:
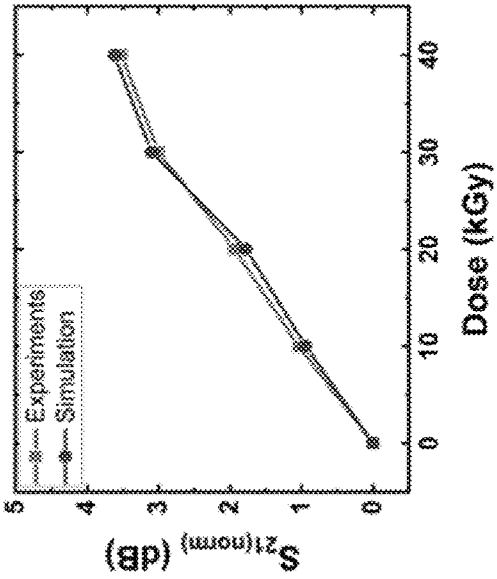

FIG. 8A-F illustrate simulation and experimental results from wireless measurements on the radiation sensor. FIG. 8A illustrates the simulation environment and a simulated depiction of the radiation pattern of the sensor. FIG. 8B illustrates $S_{21}$ as a function of frequency for various radiation doses obtained from simulations. FIG. 8C illustrates $S_{21(norm)}$ as a function of the radiation doses for various percentages of PU obtained from simulations. FIG. 8D illustrates a photograph of the experimental setup showing the reader antenna and the sensor in an anechoic chamber. FIG. 8E illustrates $S_{21}$ as a function of frequency for various radiation doses obtained from experiments. FIG. 8F illustrates a comparative analysis of $S_{21(norm)}$ as a function of the radiation dose between experiments and simulations.

FIG. 8A represents the simulation environment and the radiation pattern of the chipless radiation sensor. The radiation pattern illustrated that the highest amount of radiation was propagated from the center of the chipless tag with the main lobe magnitude of −10 dB. Based on the point where the radiation intensity reduces by 3 dB, the simulation returned an angular width of 52° indicating a reasonable detection range for the sensor in terms of the angular alignment. The simulation results shown in FIG. 8*b* feature $S_{21}$, which is the ratio of the power backscattered from the sensor tag and collected by the reader antenna to the power radiated by the reader antenna to cause backscattering, as a function of the frequency. Since the sensing tag and the reference tag have different lengths, separate resonant peaks were obtained for each tag and were illustrated on the $S_{21}$ vs frequency spectra. The resonant frequency of the sensing tag ($f_s$) was observed at ~1.36 GHz and the resonant frequency of the reference tag ($f_r$) was observed at ~3.15 GHz. A 3-fold reduction in the length of the reference tag with respect to the length of the sensing tag has provided a 2.3-fold increase in the corresponding resonant frequencies which prevented resonant peaks from overlapping. When the radiation dose was 0 kGy, the conductivity of the PEDOT: PSS layer was 0.03 S/m, and the amplitude of the peak at the resonant frequency of the sensing tag ($S_{21|f=f_s}$) was −41.84 dB and the amplitude of the peak at the resonant frequency of the reference tag ($S_{21|f=f_r}$) was −33.63 dB. As the radiation dose was increased, the resistance of the PEDOT: PSS layer got corresponding increased which led to an increase in $S_{21}|f=f_s$. Two microstrip lines separated by a dielectric material provide the best backscattering when they act as an ideal open circuit and show a reduction in the magnitude of reflections the farther the resistance of the dielectric material is from an open circuit scenario insofar as the resistance is not too low to create a short circuit scenario. Consequently, the increase in $S_{21|f=f_s}$ in response to an increase in the resistance of the PEDOT: PSS layer was a result of the sensor tag moving toward becoming an ideal open circuit. This trend was exemplified in FIG. 8B where $S_{21|f=f_s}$ was increased from −41.48 dB to −40.86 dB, −40.022 dB, and −38.7 dB when the radiation dose was increased from 0 kGy to 10 kGy, 20 kGy, 30 kGy, and 40 kGy, respectively. However, the variation observed in $S_{21|f=f_r}$ was negligible as the PEDOT: PSS layer was only present on the sensing tag. The magnitude of resonance of the sensing tag was normalized with respect to the magnitude of resonance of the reference tag and is illustrated in FIG. 8*c*. The normalized value of $S_{21}$ was represented as $S_{21(norm)}$ and was plotted for various percentages of PU. When PUwt % is 50 wt % and 70 wt %, the variation in $S_{21(norm)}$ when the radiation dosage was changed from 0 kGy to 40 kGy was under 2 dB. Moreover, the radiation sensitivity obtained with a linear fit was only 0.0246 dB/kGy and 0.0393 dB/kGy for 50 wt % and 70 wt % PU percentages, respectively and were too close to the noise margin to obtain distinguishable readings. In contrast, at a radiation dosage of 80 wt %, $S_{21(norm)}$ was increased by 2.52 dB when the radiation dosage was increased from 0 kGy to 30 kGy. However, the radiation sensitivity extracted with a linear fit was 0.084 dB/kGy up to 30 kGy which further decreased as the dosage was approaching 40 kGy. When the percentage of PU was set to 90 wt %, $S_{21(norm)}$ was increased by 3.1 dB when the radiation dosage was increased from 0 kGy to 30 kGy. Consequently, at 90 wt % PU, we obtained a radiation sensitivity of 0.1033 dB/kGy up to 30 kGy and a trend toward plateauing beyond 30 kGy. Since a minimum radiation sensitivity of 1 dB/kGy is required to obtain discernable reflections from the sensor tag among the noise from the background, 90 wt % PU is the optimum material setting required for the reliable chipless wireless radiation sensor.

Next, the wireless measurements were performed in an anechoic chamber using sensors manufactured with the optimum material setting of 90 wt % PU (FIG. 8*d*).

FIG. 8*d* shows a cross-polarized horn antenna that acts as the reader and is connected to a vector network analyzer for the measurements. A Vector Network Analyzer (VNA) was used for generating the RF signals fed into the antenna for transmission and for analyzing the signals received by the reader antenna.

FIG. 8*e* shows the experimental results obtained from the anechoic chamber for various values of radiation dosage on the sensor. Two distinguishable resonant peaks were obtained for the sensing tag and the reference tag for all the radiation dosages. In the experiments, $f_r$ was observed at ~3.13 GHz which closely aligned with the $f_r$ obtained from the simulations (3.15 GHz). The sensing tag resonated around 1.295 GHz with $f_s$ showing a 2.7% standard deviation caused by the variation in the phase angle of the dielectric constant of PEDOT: PSS over time. However, $S_{21|f=f_s}$ demonstrated a trend similar to the one observed in simulations. When the radiation dose was 0 kGy, $S_{21|f=f_s}$ was −41.872 dB and $S_{21|f=f_r}$ was −33.63 dB. When the radiation dose was systematically increased from 0 kGy to 10 kGy, 20 kGy, and 30 kGy, $S_{21|f=f_s}$ gradually increased from −41.872 dB to −40.836 dB, −39.866 dB, −38.89 dB, respectively. As expected, $S_{21|f=f_r}$ demonstrated a negligible deviation from −33.63 dB with a standard deviation of merely 0.1 dB indicating the reference tag's resilience to gamma radiation. When the radiation dosage was increased to 40 kGy, $S_{21|f=f_s}$ increases to −38.34 dB with a reduction in the sensitivity due to the plateauing effect demonstrated by resistance measurements.

FIG. 8F demonstrates the comparative analysis of $S_{21(norm)}$ between the experimental results and the simulation results obtained after normalizing $S_{21|f=f_s}$ with respect to $S_{21|f=f_r}$. The experimental studies revealed that $S_{21(norm)}$ increased gradually from 0 dB to 1.042 dB, 1.94 dB, and 3 dB as the radiation dosage was increased from 0 kGy to 10 kGy, 20 kGy, and 30 kGy, respectively. In the region between 0 kGy to 30 kGy, the sensing tags provided a radiation sensitivity of 0.1 dB/kGy from the experiments which closely matches the radiation sensitivity of 0.1033 dB/kGy obtained from simulations. When the radiation dosage was increased to 40 kGy, the radiation sensitivity reduced from 0.1 dB/kGy to 0.052 dB/kGy in experiments and from 0.1033 dB/kGy to 0.052 dB/kGy in simulations corroborating the plateauing effect observed in resistance measurements.

The system and methods described herein provide a printed radiation sensor that measures gamma radiation exposure in real-time by means of wireless far-field technology. The developed wireless radiation sensors may be manufactured by low-cost scalable printing technologies allowing the use of individual radiation sensors inside packaged medical devices thereby improving trackability and quality control in industrial radiation sterilization processes. PEDOT:PSS/PU composites with conductive properties in the percolation transition area were more sensitive to gamma radiation, reaching about 375% in relative impedance change at 40 kGy (90 wt % PU composites). This sensitivity to radiation exposure was attributed to the weak connectivity among conductive pathways within the composite that upon radiation exposure were easily disrupted leading to a significant decline in conductivity. The various experimentation, though not limiting to the scope of the system and methods described herein, demonstrate a printed chipless radiation sensor working in a differential configuration that can be wirelessly read from a distance of approximatly 10 cm. The radiation sensor manufactured with 90 wt % PU composites provided an amplitude shift of 3.1 dB with a linear radiation sensitivity of 0.1 dB/kGy in the range of 0-40 kGy. The printed radiation sensor presented in this work has potential applications in the sterilization of medical devices and drugs, food, agricultural products, and other industries.

Experimental Section/Methods

The experimental setup was performed according to the following guidelines. The following guidelines are intended to exemplify various embodiments that are possible by the system and methods described herein.

Synthesis of PEDOT: PSS/PU Composites: PEDOT: PSS/PU solutions were prepared by mixing an aqueous emulsion of PEDOT: PSS (Sigma Aldrich, 0.5 wt. % PEDOT content and 0.8 wt. % PSS content) and a waterborne polyurethane dispersion (Alberdingk Boley U3200, 31-30 wt. % solid content) at different ratios to obtain the following composites: 30 wt. % PEDOT:PSS-70 wt. % PU, 50 wt. % PEDOT:PSS-50 wt. % PU, 70 wt. % PEDOT:PSS-30 wt. % PU, 80 wt. % PEDOT:PSS-20 wt. % PU, 90 wt. % PEDOT:PSS-10 wt. % PU and 95 wt. % PEDOT:PSS-5 wt. % PU To avoid the agglomeration of suspended PU particles in the highly acidic PEDOT:PSS emulsion (pH of 1.2), PEDOT:PSS emulsion was neutralized prior to mixing by the slow addition of 1 M of NAOH until reaching a pH of 7. Each composite solution was mechanically stirred at 500 rpm for 5 minutes before casting.

Fabrication of printed wireless radiation sensors: The printed radiation sensors were manufactured employing the following steps. First, an acrylic substrate sheet was cut in 10 cm×10 cm rectangular substrates by using a $CO_2$ laser engraving system (PLS6MW, ULS, Inc.) at 15 W power and 10 mm/s speed. Next, a 10 cm×10 cm copper tape was manually attached to the backside of the acrylic substrate. The reference and sensor tags were made of DuPont 5025 silver paste and printed onto polyethylene terephthalate (PET) sheets with an MPS TF-100 screen printer. The sensing tag was designed as a straight strip of printed silver of 5 mm width, 90 mm length, and 20 μm thickness. An interdigitated circular area to deposit the sensing material was included in the center of the tag having 12 mm diameter and 0.6 mm digits equally spaced 0.6 mm. Similarly, the reference tag was designed as a rectangular strip of 5 mm width, 40 mm length, and 20 μm thickness. Both, the reference and IDE structure of the sensing tag were dried in an oven at 120° C. for 5 min and manually attached to the acrylic substrate. Next, the reference and sensor tag was placed inside a PE-25 plasma etching system to improve substrate adhesion by plasma treatment. The plasma treatment was carried out for 45 seconds at 200 W power. Next, 50 μL of PEDOT: PSS/PU solution was cast onto the interdigitated area of the sensor tag and dried at 50° C. in a hot plate for 50 seconds at lab conditions (20° C. and 40% RH). After drying, composite films were formed having about 30 μm in thickness. Finally, the tag and reference sensor were passivated by Silicone (Heat Cure RTV Adhesive Coating, Silicone Solutions) creating a passivation layer of about 120 μm thickness after drying at lab conditions.

Characterization: The morphology of PEDOT: PSS/PU composites were investigated by optical microscopy. A small amount of each composite was doctor bladed on glass slides and examined with a LEITZ LABORLUX 12 POL microscope and 32× magnification lens. Micrographs were recorded with an IMAGING camera attached to the microscope and analyzed by IMAGE-Pro Software. The initial impedance of PEDOT: PSS/PU composites was characterized by preparing screen-printed electrodes with the same interdigitated area as the described sensor tags and casting 50 μL of each solution. The impedance of three samples was measured before and after silicone passivation with an LCR meter (LCR-821, GW Instek) at 1 kHz frequency and 0.1 V amplitude voltage. The adhesion between PEDOT: PSS/PU films and the substrate (PET), was investigated by a peeling test. A strip of pressure-sensitive (ASTM D3330 tape) was attached to the surface of cast films on silver-printed electrodes. Next, the attached tape was continuously peeled away keeping a 90° angle between the strip and the substrate. The peeling test was performed in three samples for each composite. Since small concentrations of NaOH were added for the preparation of composites, neutralized PEDOT: PSS was used as a reference in this test. Changes in the chemical structure of PEDOT: PSS and PU induced by gamma radiations were investigated through Attenuated Total Reflection Fourier Transform Infrared Spectroscopy (ATR-FTIR, PerkinElmer Spectrum 100 FTIR Spectrometer) in the range from 4000 $cm^{-1}$ to 650 $cm^{-1}$.

Radiation and sensitivity measurements: Radiation experiments were carried out with a gamma radiation source (Gamma Cell 220 from Atomic Energy of Canada). Three sensor tags for each composite were placed inside the gamma irradiator and continuously irradiated at a rate of 2 kGy/day. Impedance measurements were performed by using an LCR meter (LCR-821, GW Instek) at 1 kHz frequency and 0.1 V amplitude voltage. All sensors were read when reached the following radiation doses: 0 kGy, 10 kGy, 20 kGy, 25 kGy, 30 kGy, 35 kGy, and 40 kGy. Sensitivity was reported in terms of relative impedance change in the range from 0 kGy to 40 kGy calculated with the following equation, where $Z_0$ is the impedance of the radiation sensors before radiation exposure while Z represents the impedance read at a particular radiation dose.

$$\frac{\Delta Z}{Z_0}(\%) = \left(\frac{Z - Z_0}{Z_0}\right) * 100\%$$

Wireless Measurements: The experiments on the wireless radiation sensor were conducted in an ETS-Lindgren's Anechoic Chamber with a cross-polarized reader antenna that can operate from 300 MHz to 12 GHz with a gain of 7 dBi. The vertical ridge of the reader antenna is used for transmitting vertically polarized RF signals to the sensor whereas the horizontal ridge is used for receiving horizontally polarized backscattered signals from the sensor. A cross-polarized antenna helps in reducing the noise from the background as the reflected signals from the background are mostly vertically polarized and are less likely to interfere with the horizontally polarized reflections from the sensor tag. The VNA used for the measurements is Keysight E5072A that can operate from 30 KHz to 8.5 GHz while easily covering the working range of the wireless radiation sensor.

The system may be implemented with additional, different, or fewer components than illustrated. Each component may include additional, different, or fewer components.

Figure 9:
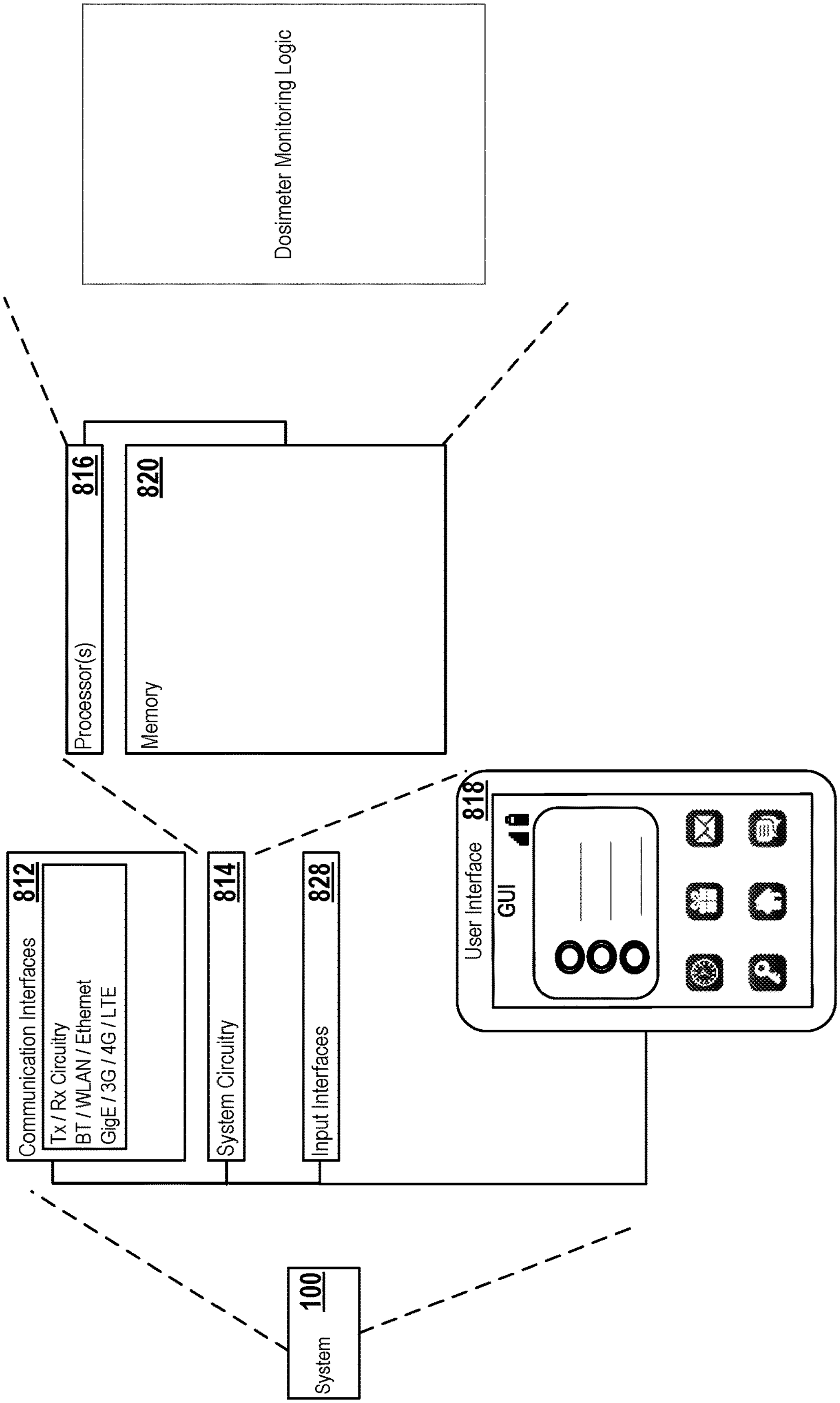
FIG. 9 illustrates a second example of a system.

FIG. 9 illustrates a second example of the system 100. The system 100 may include communication interfaces 812, input interfaces 828, system circuitry 814, the network analyzer 104, and/or the antenna 105. The system circuitry 814 may include a processor 816 or multiple processors. Alternatively or in addition, the system circuitry 814 may include memory 820.

The processor 816 may be in communication with the memory 820. In some examples, the processor 816 may also be in communication with additional elements, such as the communication interfaces 812, the input interfaces 828, and/or the user interface 818. Examples of the processor 816 may include a general processor, a central processing unit, logical CPUs/arrays, a microcontroller, a server, an application specific integrated circuit (ASIC), a digital signal processor, a field programmable gate array (FPGA), and/or a digital circuit, analog circuit, or some combination thereof.

The processor 816 may be one or more devices operable to execute logic. The logic may include computer executable instructions or computer code stored in the memory 820 or in other memory that when executed by the processor 816, cause the processor 816 to perform the operations the dosimeter monitoring logic and/or other operations described herein. The computer code may include instructions executable with the processor 816.

The memory 820 may be any device for storing and retrieving data or any combination thereof. The memory 820 may include non-volatile and/or volatile memory, such as a random access memory (RAM), a read-only memory (ROM), an erasable programmable read-only memory (EPROM), or flash memory. Alternatively or in addition, the memory 820 may include an optical, magnetic (hard-drive), solid-state drive or any other form of data storage device. The memory 820 may include at least one of the dosimeter monitoring logic and/or logic for other operations described herein.

The user interface 818 may include any interface for displaying graphical information. The system circuitry 814 and/or the communications interface(s) 812 may communicate signals or commands to the user interface 818 that cause the user interface to display graphical information. Alternatively or in addition, the user interface 818 may be remote to the system 100 and the system circuitry 814 and/or communication interface(s) may communicate instructions, such as HTML, to the user interface to cause the user interface to display, compile, and/or render information content. In some examples, the content displayed by the user interface 818 may be interactive or responsive to user input. For example, the user interface 818 may communicate signals, messages, and/or information back to the communications interface 812 or system circuitry 814.

The system 100 may be implemented in many different ways. In some examples, the system 100 may be implemented with one or more logical components.

For example, the logical components of the system 100 may be hardware or a combination of hardware and software. The logical components may include the radiation sensor monitoring component, or any component or subcomponent of the system 100 which perform operations described herein. In some examples, each logic component may include an application specific integrated circuit (ASIC), a Field Programmable Gate Array (FPGA), a digital logic circuit, an analog circuit, a combination of discrete circuits, gates, or any other type of hardware or combination thereof. Alternatively or in addition, each component may include memory hardware, such as a portion of the memory 820, for example, that comprises instructions executable with the processor 816 or other processor to implement one or more of the features of the logical components. When any one of the logical components includes the portion of the memory that comprises instructions executable with the processor 816, the component may or may not include the processor 816. In some examples, each logical component may just be the portion of the memory 820 or other physical memory that comprises instructions executable with the processor 816, or other processor(s), to implement the features of the corresponding component without the component including any other hardware. Because each component includes at least some hardware even when the included hardware comprises software, each component may be interchangeably referred to as a hardware component.

Some features are shown stored in a computer readable storage medium (for example, as logic implemented as computer executable instructions or as data structures in memory). All or part of the system and its logic and data structures may be stored on, distributed across, or read from one or more types of computer readable storage media. Examples of the computer readable storage medium may include a hard disk, a floppy disk, a CD-ROM, a flash drive, a cache, volatile memory, non-volatile memory, RAM, flash memory, or any other type of computer readable storage medium or storage media. The computer readable storage medium may include any type of non-transitory computer readable medium, such as a CD-ROM, a volatile memory, a non-volatile memory, ROM, RAM, or any other suitable storage device.

The processing capability of the system may be distributed among multiple entities, such as among multiple processors and memories, optionally including multiple distributed processing systems. Parameters, databases, and other data structures may be separately stored and managed, may be incorporated into a single memory or database, may be logically and physically organized in many different ways, and may implemented with different types of data structures such as linked lists, hash tables, or implicit storage mechanisms. Logic, such as programs or circuitry, may be combined or split among multiple programs, distributed across several memories and processors, and may be implemented in a library, such as a shared library (for example, a dynamic link library (DLL).

All of the discussion, regardless of the particular implementation described, is illustrative in nature, rather than limiting. For example, although selected aspects, features, or components of the implementations are depicted as being stored in memory(s), all or part of the system or systems may be stored on, distributed across, or read from other computer readable storage media, for example, secondary storage devices such as hard disks, flash memory drives, floppy disks, and CD-ROMs. Moreover, the various logical units, circuitry and screen display functionality is but one example of such functionality and any other configurations encompassing similar functionality are possible.

The respective logic, software or instructions for implementing the processes, methods and/or techniques discussed above may be provided on computer readable storage media. The functions, acts or tasks illustrated in the figures or described herein may be executed in response to one or more sets of logic or instructions stored in or on computer readable media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one example, the instructions are stored on a removable media device for reading by local or remote systems. In other examples, the logic or instructions are stored in a remote location for transfer through a computer network or over telephone lines. In yet other examples, the logic or instructions are stored within a given computer and/or central processing unit ("CPU").

Furthermore, although specific components are described above, methods, systems, and articles of manufacture described herein may include additional, fewer, or different components. For example, a processor may be implemented as a microprocessor, microcontroller, application specific integrated circuit (ASIC), discrete logic, or a combination of other type of circuits or logic. Similarly, memories may be DRAM, SRAM, Flash or any other type of memory. Flags, data, databases, tables, entities, and other data structures may be separately stored and managed, may be incorporated into a single memory or database, may be distributed, or may be logically and physically organized in many different ways. The components may operate independently or be part of a same apparatus executing a same program or different programs. The components may be resident on separate hardware, such as separate removable circuit boards, or share common hardware, such as a same memory and processor for implementing instructions from the memory. Programs may be parts of a single program, separate programs, or distributed across several memories and processors.

A second action may be said to be "in response to" a first action independent of whether the second action results directly or indirectly from the first action. The second action may occur at a substantially later time than the first action and still be in response to the first action. Similarly, the second action may be said to be in response to the first action even if intervening actions take place between the first action and the second action, and even if one or more of the intervening actions directly cause the second action to be performed. For example, a second action may be in response to a first action if the first action sets a flag and a third action later initiates the second action whenever the flag is set.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

While various embodiments have been described, it will be apparent to those of ordinary skill in the art that many more embodiments and implementations are possible.

Accordingly, the embodiments described herein are examples, not the only possible embodiments and implementations.

What is claimed is:

1. A method comprising:

receiving a package previously irradiated for sterilization, the package having a sensor comprising a reference tag and a sensing tag, the sensing tag at least partially coated with a material comprising poly(3,4-ethylenedioxythiophene) polystyrene sulfonate (PEDOT:PSS) and Polyurethane (PU), wherein the resonant frequency of the sensing tag is different from the resonant frequency of the reference tag;

scanning the sensing tag and the reference tag during a same interrogation operation;

measuring a first peak amplitude of a reflected power from the sensing tag at the resonant frequency of the sensing tag;

measuring a second peak amplitude of a reflected power from the reference tag at the resonant frequency of the reference tag; and outputting, based on a comparison of the first peak amplitude at the resonant frequency of the sensing tag and the second peak amplitude at the resonant frequency of the reference tag, a quality measure indicative of the sensor being exposed to radiation.

2. The method of claim 1, wherein outputting a quality measure indicative of whether the sensor was exposed to radiation further comprises:

displaying the information, communicating the information, storing the information in memory, or a combination thereof.

3. A method, comprising:

printing a reference tag and a sensing tag onto a substrate, the sensing tag having an interdigitated electrode (IDE), the reference tag and sensing tag not touching; and coating the IDE of the sensing tag with poly(3,4-ethylenedioxythiophene) polystyrene sulfonate (PEDOT:PSS) and Polyurethane (PU), wherein the sensing tag and the reference tag are dimensioned to have isolated resonant frequencies to provide distinct resonant responses.

4. The method of claim 3, wherein the substrate isa first substrate, the method further comprising applying the first substrate to a second substrate.

5. The method of claim 4, wherein the first substrate is a polyethylene terephthalate (PET) sheet and the second substrate is an acrylic sheet.

6. The method of claim 4, further comprising plasma etching the combined first and second substrates.

7. The method of claim 4, further comprising applying a metallic tape to the second substrate.

8. The method of claim 3, further comprising covering the sensing tag and reference tag with a passivation layer.

9. The method of claim 8, wherein the passivation layer comprises silicone.

10. A radiation sensor, comprising:

a substrate;

a reference tag located on a surface of the substrate; and a sensing tag located on the surface of the substrate separate from the reference tag, the sensing tag having an interdigitated electrode (IDE) coated in a radiation sensitive material which causes conductivity across the interdigitated electrode to decrease in response to exposure to radiation, wherein the sensing tag and the reference tag are dimensioned to have isolated resonant frequencies to provide distinct resonant responses.

11. The radiation sensor of claim 10, wherein the radiation sensitive material comprises poly(3,4-ethylenedioxythiophene) polystyrene sulfonate (PEDOT:PSS) and Polyurethane (PU).

12. The radiation sensor of claim 10, wherein the reference tag comprises an electrode.

13. The radiation sensor of claim 10, wherein the substrate comprises an acrylic layer and a PET layer, wherein the reference tag and sensing tag are disposed on the PET layer.

14. The radiation sensor of claim 10, wherein the reference tag comprises silver.

15. The radiation sensor of claim 10, wherein the interdigitated electrode comprises silver.

* * * * *